United States Patent [19]

Stillings

[11] 4,446,148

[45] May 1, 1984

[54] BENZODIOXANYL IMIDAZOLINE COMPOUNDS, COMPOSITIONS AND USE

[75] Inventor: Michael R. Stillings, Hull, England

[73] Assignee: Reckitt & Colman Products Limited, Hull, England

[21] Appl. No.: 480,370

[22] Filed: Mar. 29, 1983

[30] Foreign Application Priority Data

Apr. 17, 1982 [GB] United Kingdom ................ 8211205

[51] Int. Cl.³ .................. A61K 31/415; C07D 405/04
[52] U.S. Cl. ................................. 424/273 R; 548/348
[58] Field of Search ...................... 548/348; 424/273 R

[56] References Cited

U.S. PATENT DOCUMENTS 2,979,511  4/1961  Krapcho et al. .................... 548/348
4,397,860  8/1983  Chapleo et al. ..................... 548/348

Primary Examiner—Robert W. Ramsuer

Attorney, Agent, or Firm—Bacon & Thomas

[57] ABSTRACT

Imidazoline derivatives of the formula

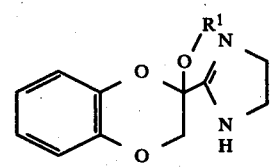

having the RS or S configuration wherein $R^1$ is alkyl $C_{1-4}$, allyl, benzyl, phenethyl or hydroxyalkyl $C_{2-4}$ and their non-toxic salts.

Processes for their preparation and pharmaceutical compositions thereof. The compounds exhibit presynaptic $\alpha_2$-adrenoreceptor antagonist activity.

11 Claims, No Drawings

BENZODIOXANYL IMIDAZOLINE COMPOUNDS, COMPOSITIONS AND USE

This invention relates to imidazoline derivatives their non-toxic salts, processes for their preparation and pharmaceutical compositions of the derivatives or their salts.

According to this invention there are provided compounds of the formula

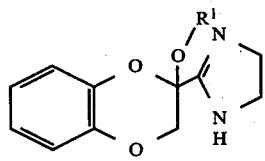

wherein $R^1$ is alkyl $C_{1-4}$, allyl, benzyl, phenethyl or hydroxyalkyl $C_{2-4}$ and their non-toxic salts having the RS or S configuration.

Suitable values of $R^1$ include methyl, ethyl, n-propyl, i-propyl, n-butyl, allyl, benzyl, phenethyl, hydroxyethyl, hydroxypropyl and hydroxybutyl.

The invention also includes pharmaceutical compositions comprising a compound of formula I or a non-toxic salts thereof, as defined above together with a pharmaceutically acceptable diluent or carrier.

Examples of non-toxic salts are those with inorganic acids such as hydrochloric acid, sulphuric or phosphoric acid; or organic acids such as acetic, propionic, malonic, succinic, fumaric, tartaric, citric or cinnamic acid. A preferred salt is the hydrochloride.

The compounds of formula I exhibit $\alpha_2$-adrenoreceptor antagonist activity and thus have potential in the treatment of depression. Other conditions in which $\alpha_2$-adrenoreceptor antagonists may be used include cardiac diseases, excessive bronchoconstriction (as in asthma and hay fever), metabolic disorders (such as diabetes and obesity) and migraine.

The invention also includes the use of a compound of formula I or a non-toxic salt thereof in the treatment of depression and a method of treating depression which comprises administering to humans an antidepressant effective amount of a compound of formula I or a non-toxic salt thereof.

The compounds of formula I in the RS configuration may be prepared from the compounds of formula II

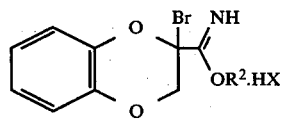

where $R^2$ is alkyl $C_{1-4}$ and HX is an acid (preferably a pharmaceutically acceptable acid) by treatment with at least molar equivalents of ethylenediamine and an alcohol of formula $R^1OH$ wherein $R^1$ is as hereinbefore defined. Preferably the reaction is carried out employing an excess of the alcohol $R^1OH$, where the alcohol serves as a solvent for the reaction, at a temperature in the range 0°–25° C. Preferably HX is hydrogen chloride and $R^2$ is methyl or ethyl.

The compounds of formula II may be prepared from the analogous cyano compound of formula III

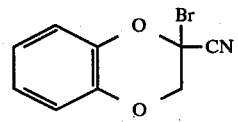

by treatment with an alcohol of formula $R^2OH$, wherein $R^2$ is as hereinbefore defined, in the presence of an acid HX where HX is as hereinbefore defined. Most conveniently the alcohol is methanol or ethanol and HX is hydrogen chloride, the reaction being carried out in anhydrous diethyl ether as solvent.

A particularly convenient method of carrying out the process for compounds where $R^1$ is alkyl $C_{1-4}$ or allyl is to generate the compounds of formula II (in which, for this method $R^1=R^2$) in situ from the cyano compound of formula III. Thus for example the cyano compound of formula III dissolved in an alcohol of formula $R^1OH$ (wherein $R^1$ is alkyl $C_{1-4}$ or allyl) is treated with a catalytic amount of a sodium alkoxide (conveniently sodium methoxide) followed by reaction with hydrogen chloride (dissolved in an alcohol $R^1OH$ or more conveniently diethyl ether) and at least one molar equivalent of ethylenediamine.

The cyano compound of formula III may be prepared from the compound of formula IV

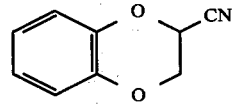

by bromination, in a non-polar solvent such as carbon tetrachloride, using N-bromosuccinimide with a catalytic quantity of a radical initiator such as 2,2'-azobis-(2-methylpropionitrile).

The compounds of formula I obtained as racemic mixtures may be resolved using standard procedures. Thus for example the compound of Example 1 wherein $R^1$ is methyl was resolved via its dibenzoyl tartrate salts using fractional crystallization. Basification of the two diastereoisomeric salts gave the enantiomeric bases which were converted to their hydrochloride salts. Testing results indicated that all the activity resided in the (+) enantiomer and subsequent X-ray studies revealed that the active isomer had the S configuration.

The invention is illustrated by the following Examples in which temperatures are in degrees Celsius. The various compounds and intermediates were examined by thin layer chromatography (t.l.c.) on silica gel plates (Merck, Kieselgel 60 $F_{254}$). Melting points were determined on a Kofler hot stage apparatus or a Buchi apparatus in glass capillary tubes and are uncorrected. I.R. spectra were recorded on a Perkin-Elmer 710 B spectrophotometer.

EXAMPLE 1

2-[2-(2-Methoxy-1,4-benzodioxanyl)]-2-imidazoline (a) 2-Bromo-2-cyano-1,4-benzodioxan A stirred mixture of 2-cyano-1,4-benzodioxan (15 g), N-bromosuccinimide (16.5 g), 2,2'-azobis-(2-methylpropionitrile) (0.2 g) in carbon tetrachloride (400 ml) was heated under reflux for 14 hr. The mixture was cooled and the precipitated succinimide removed. Evaporation gave an oil which was purified by column chromatography (Kieselgel 60, 70-230 mesh/petroleum ether bpt. 40°-60°) to give the bromo-nitrile (19 g); NMR (CDCl$_3$) δ7.0 (4H, s, Ar-H), 4.5 (2H, ABq, J=10 Hz, —CH$_2$—).

(b) Ethyl[2-(2-bromo-1,4-benzodioxanyl)]-imidoate hydrochloride

A slow stream of hydrogen chloride gas was passed through a solution of the above bromo-nitrile (5.0 g) and ethanol (1.16 ml) in dry diethyl ether (150 ml) at 0°-5° for 0.5 hr. The reaction mixture was then kept at 0° for 14 hr, after which the crystalline imidoate salt was filtered off, washed with dry diethyl ether and dried (5.3 g) I.R. ν$_{max}$ 2750, 1670 cm$^{-1}$.

(c) 2-[2-(2-Methoxy-1,4-benzodioxanyl)]-2-imidazoline

A suspension of the above imidoate hydrochloride (1.3 g) in dry methanol (7.5 ml) was stirred and cooled at 0°-5° during the dropwise addition of ethylenediamine (0.325 ml). The resultant solution was stirred at room temperature for 2 hr before pouring into a saturated solution of sodium bicarbonate. The aqueous layer was extracted with methylene chloride which was dried and evaporated to yield a solid. Purification via column chromatography (Kieselgel 60, 70-230 mesh/methylene chloride—2% v/v methanol) gave pure 2-[2-(2-methoxy-1,4-benzodioxanyl)]-2-imidazoline (0.25 g) m.p. 90°-91°. NMR (CDCl$_3$) δ7.0 (4H, s, Ar-H), 5.0 (1H, broad s, —N—H), 4.3 (2H, ABq, J=11 Hz, —CH$_2$—), 3.8 (4H, s, N—CH$_2$CH$_2$—N), 3.4 (3H, s, —OCH$_3$).

EXAMPLE 2

2-[2-(2-Methoxy-1,4-benzodioxanyl)]-2-imidazoline

A solution of 2-bromo-2-cyano-1,4-benzodioxan (3.0 g) in dry methanol (60 ml) was cooled to 0° C. and sodium methoxide (100 mg) was added. After stirring the solution at 0°-10° for 15-30 min., ethylenediamine (0.825 g) was added followed by dropwise addition over 2 min. of methanolic HCl (5 M, 3 ml). The solution was stirred for a further 30 min. at 0°-10° and then allowed to warm to room temperature and stirred for 3 hr. The reaction was then worked-up by the method of Example 1(c) to give pure material, as determined by t.l.c., (2.7 g) identical to the product of Example 1.

The following Examples 3 to 11 were prepared by the method of Example 1 using the appropriate alcohol R$^1$OH in place of methanol in step c. It will be appreciated that according to the method of preparation the compounds of Examples 1 to 11 will be obtained in the racemic or RS configuration.

TABLE

| Example | R$^1$ | m.p. | Yield | % Calculated % Found | | | Formula |
|---|---|---|---|---|---|---|---|
| | | | | C | H | N | |
| 3 | —Et | 206–210 | 43 | 53.98 | 6.10 | 9.69 | C$_{13}$H$_{16}$N$_2$O$_3$HCl.¼H$_2$O |
| | | | | 53.70 | 5.91 | 9.62 | |
| 4 | n-Pr | 95–97 | 22 | 64.10 | 6.92 | 10.68 | C$_{14}$H$_{18}$N$_2$O$_3$ |
| | | | | 63.89 | 7.13 | 10.40 | |
| 5 | i-Pr | 100–102 | 19 | 63.02 | 6.99 | 10.50 | C$_{14}$H$_{18}$N$_2$O$_3$¼H$_2$O |
| | | | | 63.31 | 7.15 | 10.41 | |
| 6 | n-Bu | 92–93 | 24 | 65.20 | 7.30 | 10.14 | C$_{15}$H$_{20}$N$_2$O$_3$ |
| | | | | 65.13 | 7.37 | 10.06 | |
| 7 | allyl | 73–76 | 55 | 64.60 | 6.20 | 10.76 | C$_{14}$H$_{16}$N$_2$O$_3$ |
| | | | | 64.20 | 6.20 | 10.60 | |
| 8 | —CH$_2$Ph | 139–141 | 16 | 68.34 | 5.95 | 8.86 | C$_{18}$H$_{18}$N$_2$O$_3$½H$_2$O |
| | | | | 68.18 | 5.82 | 8.72 | |
| 9 | —(CH$_2$)$_2$Ph | 165–166 | 57 | 63.24 | 5.87 | 7.76 | C$_{19}$H$_{20}$N$_2$O$_3$HCl |
| | | | | 63.17 | 5.94 | 7.64 | |
| 10 | —(CH$_2$)$_2$OH | 142–145 | 41 | 59.08 | 6.10 | 10.60 | C$_{13}$H$_{16}$N$_2$O$_4$ |
| | | | | 59.20 | 6.46 | 10.41 | |
| 11 | —(CH$_2$)$_4$OH | * | 29 | | | | |

*product obtained as the free base was an oil, R$_f$ 0.56 (chloroform/methanol 4:1 v/v).

Resolution of 2-[2-(2-methoxy-1,4-benzodioxanyl)]-2-imidazoline

A solution of racemic 2-[2-(2-methoxy-1,4-benzodioxanyl)]-2-imidazoline (8.8 g) in hot acetone (250 ml) was added to a solution of (+)-dibenzoyl-d-tartaric acid monohydrate (14.08 g) in hot acetone (250 ml). The clear solution obtained was decanted from an insoluble residue and allowed to cool to room temperature. A precipitate of the dibenzoyl tartrate salt was filtered off, washed with diethyl ether and dried to give 19.2 g of a white solid. [α]$_D$= +81.6° (C=1.00, methanol). Recrystallisation of this sample from methanol (250 ml)/ethyl acetate (500 ml) on cooling gave 11.5 g of the salt with [α]$_D$= +99.5° (C=1.01, methanol). Two further recrystallisations from hot methanol (220 ml) gave 4.5 g of the salt whose optical rotation [α]$_D$= +114° (C=1.01, methanol) was unchanged upon further recrystallisation.

A suspension of the optically pure salt (3.9 g) in methylene chloride (150 ml) was treated with a solution of potassium carbonate (30 g) in water (100 ml). The mixture was stirred at room temperature for 30 min. and the organic phase was separated and combined with two further extractions of the aqueous phase. Drying and removal of the solvent gave 2-[2-(2-methoxy-1,4-benzodioxanyl)]-2-imidazoline 1.2 g [α]$_D$= +101.5° (C=1.01, methanol) m.p. 102°-104°.

300 mg of the free base was dissolved in diethyl ether and a solution of ethereal-HCl was added. The HCl salt was filtered off washed with diethyl ether and dried. Yield 240 mg [α]$_D$= +96.2° (C=1.0, methanol) m.p. 283°-285°.

Analysis C$_{12}$H$_{15}$ClN$_2$O$_3$ requires C, 53.24; H, 5.58; N, 10.35; found C, 52.84; H, 5.66; N, 10.13.

The HBr salt was obtained in a similar manner and X-ray crystallographic studies established that the compound had the S configuration.

An identical procedure was used to prepare the HCl salt of the (−)-2-[2-(2-methoxy-1,4-benzodioxanyl)]-2-imidazoline, using (−) dibenzoyl-l-tartaric acid.

The pharmacological activity of the compounds of the invention have been determined according to the following procedures.

1. Pre- and postsynaptic α-adrenoreceptor antagonism in isolated tissue experiments Presynaptic $\alpha_2$-adrenoreceptor antagonism was assessed by determining pA$_2$ values against the inhibitory effects of clonidine, a well known presynaptic $\alpha_2$-adrenoreceptor agonist, on the rat vas deferens stimulated at a frequency of 0.1 Hz according to the method of Doxey, J. C., Smith, C. F. C., and Walker, J. M., Br. J. Pharmac., 1977, 60, 91.

This in vitro model is particularly useful as an initial screen for studying presynaptic activity in isolation since the physiological nature of the vas deferens tissue is such that the postsynaptic receptors located therein are particularly inaccessible to exogenous agents. In consequence an alternative tissue, the rat anococcygeus muscle is used to establish postsynaptic $\alpha_1$-adrenoreceptor activity. Antagonism of noradrenaline contractions is used to determine pA$_2$ values at postsynaptic $\alpha_1$-adrenoreceptors. The ratio of presynaptic $\alpha_2$-adrenoreceptor antagonism (versus clonidine on the rat vas deferens) to postsynaptic $\alpha_1$-adrenoreceptor antagonism (versus noradrenaline contractions on the rat anococcygeus muscle) is used to assess adrenoreceptor selectivity. Table 2 presents the results obtained with 2-[2-(2-methoxy-1,4-benzodioxanyl)]-2-imidazoline (Example 1), 2-[2-(1,4-benzodioxanyl)]-2-imidazoline (A) and 2-[2-(2-methyl-1,4-benzodioxanyl)]-2-imidazoline (B). Table 2 also includes the results for four standard drugs: (i) the non-selective α-adrenoreceptor antagonist, phentolamine, (ii) the selective presynaptic antagonist, yohimbine, (iii) the highly selective postsynaptic antagonist, prazosin, and (IV) the antidepressant, mianserin which shows nonselective pre- and postsynaptic adrenoreceptor antagonist properties as part of its pharmacological profile.

TABLE 2

| Compound | Presynaptic antagonism pA$_2$ vs Clonidine (vas deferens) | Postsynaptic antagonism pA$_2$ vs Noradrenaline (anococcygeus) | Pre/post synaptic ratio |
|---|---|---|---|
| A | 8.5 | 6.2 | 225 |
| B | 8.6 | 5.6 | 871 |
| Example 1 | 10.1 | 7.2 | 776 |
| Phentolamine | 8.4 | 7.7 | 4.8 |
| Yohimbine | 8.2 | 6.4 | 60 |
| Prazosin | 5.9 | 8.2 | 0.005 |
| Mianserin | 7.3 | 6.6 | 5.0 |

The results are the mean of a minimum of 5 experiments.

It can be seen in Table 2 that of the compounds studied, the compound of Example 1 was the most potent presynaptic $\alpha_2$-adrenoreceptor antagonist being some 10 times as active as the analogous unsubstituted compound (A) and 10 times as active as the analogous 2-methyl compound (B) and moreover being extremely selective for presynaptic sites.

2. Presynaptic $\alpha_2$-adrenoreceptor antagonism in the pithed rat (1) Rat vas deferens-intravenous activity.

This test model extends the evaluation of presynaptic $\alpha_2$-adrenoreceptor antagonism versus clonidine on the rat vas deferens to the in vivo situation. Blood pressure and stimulation induced contractions of the vas deferens were monitored in pithed rats using the method of Brown, J., Doxey, J. C., Handley, S. and Virdee, N., Recent Advances in the Pharmacology of Adrenoceptors, Elsevier North Holland, 1978. Clonidine (100 μg/kg. i.v.) causes a prolonged pressor response and a prolonged inhibition of vas deferens contractions. The test drugs were injected intravenously in a cumulative dosing schedule and their abilities to reverse the inhibition of hypogastric nerve stimulation reflected their presynaptic antagonism. Table 3 shows the doses of antagonists which caused a 50% reversal of the inhibition of hypogastric nerve stimulation.

TABLE 3

Relative antagonist potencies at presynaptic $\alpha_2$-adrenoreceptors in the pithed rat

| Compound | i.v. dose of antagonist causing 50% reversal of clonidine block on vas deferens mg/kg |
|---|---|
| Example 1 | 0.002 |
| Yohimbine HCl | 0.86 |
| Mianserin HCl | >4.4 |
| Phentolamine mesylate | 0.12 |

The results are the mean of a minimum of 4 rats.

Under the chosen experimental conditions all of the compounds studied, with the exception of mianserin produced a complete reversal of the inhibitory effects of clonidine on hypogastric nerve stimulation. The maximum reversal seen with mianserin was 36% at a cumulative intravenous dose of 4.4 mg/kg. It can be seen from Table 3 that the compound of Example 1 is clearly the most potent presynaptic $\alpha_2$-adrenoreceptor antagonist of those studied.

The pharmacological activity of the racemic compound (RS) of Example 1 (in formula I R$^1$=methyl) has been compared with the activities of the R and S enantiomers. The procedures involved the measurement of affinities of the compounds for the $\alpha_2$-binding sites labelled by [$^3$H]-RX781094 (2-[2-(1,4-benzodioxanyl)]-2-imidazoline) in the rat cerebral cortex. It has previously been shown that the affinity of $\alpha_2$-adrenoreceptor antagonists for the cerebral $\alpha_2$-binding sites and prejunctional $\alpha_2$-adrenoreceptors of the rat vas deferens is highly correlated indicating that the receptors are pharmacologically similar (Doxey, Gadie, Lane and Tulloch, Br. J. Pharmac., 1982, 77, 531P).

Radioligand binding techniques in rat cerebral cortex

Male Sprague-Dawley rats, 250–300 g, were killed by decapitation, the brains quickly removed and the cerebral cortex dissected free from striatal tissue but including the hippocampus. Tissue was homogenized in ice-cold buffered sucrose (20 vols w/v 0.3 M sucrose in Tris/HCl buffer, 0.05 M, pH 7.4) using a Potter-type glass-teflon homogenizer. A crude synaptosomal P$_2$ fraction was prepared and the washed P$_2$-pellet was resuspended in a physiological salt solution to give a final protein concentration of about 1 mg/ml. The physiological salt solution had the following composition (nM): 118 NaCl, 4.8 KCl, 1.3 CaCl$_2$, 1.2 KH$_2$PO, 1.2 MgSO$_4$, 25 NaHCO$_3$ and was equilibrated with 95% O$_2$ and 5% CO$_2$.

A typical incubation mixture (in triplicate) contained: membrane preparation (970 ul), saturating ligand (phentolamine, 1 uM) or varying concentrations of an antagonist (10 ul), and [$^3$H]-RX 781094 (20 ul, to give a final concentration of 1 nM). Samples were incubated for 15 min at 25° C. and then rapidly filtered under vacuum through Whatman GFB filters and washed. Filters were transferred to scintillation vials and NE 260 miscellar scintillation fluid (3.5 ml) was added prior to scintillation counting (at 40% efficiency). Competition binding curves including up to eight concentrations of test antagonist were constructed and $IC_{50}$ values determined. Hill plots made from each set of data were linear with Hill coefficients (nh) dose to 1.0 and inhibitor constants (Ki values) were derived from $IC_{50}$ values.

Saturation binding studies performed separately under these conditions using a range of [$^3$H]-RX 781094 concentrations (0.1-35 nM) showed that the binding was saturable. Scatchard analysis of the data indicated the presence of a single populatation of binding sites ($B_{max}$=147±36 f moles/mg protein) with an equilibrium dissociation constant (Kp) of 4.8±1.5 nM (n=4). Table 4 presents the results obtained with the RS compound of Example 1 and the R and S enantiomers.

TABLE 4

| Compound | Steric. Form. | $\alpha_2$ Ki (nM) vs [$^3$H]-RX 781094 |
|---|---|---|
| RS | (±) racemate | 0.80 ± 0.05 |
| S | (+) isomer | 0.36 ± 0.07 |
| R | (−) isomer | 256 ± 59 |

From the results in Table 4 it can be seen that the S isomer was the active form; the R isomer being almost inactive. Furthermore the S isomer was twice as potent as the racemate.

The pharmaceutical compositions may be in a form suitable for oral, rectal or parenteral administration. Such oral compositions may be in the form of capsules, tablets, granules or liquid preparations such as elixirs, syrups or suspensions.

Tablets contain a compound of formula I or a non-toxic salt thereof in admixture with excipients which are suitable for the manufacture of tablets. These excipients may be inert diluents such as calcium phosphate, microcrystalline cellulose, lactose, sucrose or dextrose; granulating and disintegrating agents such as starch; binding agents such as starch, gelatine, polyvinylpyrrolidone or acacia; and lubricating agents such as magnesium stearate, stearic acid or talc.

Compositions in the form of capsules may contain the compound or a non-toxic salt thereof mixed with an inert solid diluent such as calcium phosphate, lactose or Kaolin in a hard gelatine capsule.

Compositions for parenteral administration may be in the form of sterile injectable preparations such as solutions or suspensions in for example water, saline or 1,3-butane diol.

For the purpose of convenience and accuracy of dosing the compositions are advantageously employed in a unit dosage form. For oral administration the unit dosage form contains from 1 to 200 mg, preferably 5 to 50 mg of the compound of formula I or a non-toxic salt thereof. Parenteral unit dosage forms contain from 0.1 to 10 mg of the compound of formula I or a non-toxic salt thereof per 1 ml of the preparation.

The invention is further illustrated by the following Examples of compositions in which all parts are by weight.

EXAMPLE I

A mixture of one part 2-[2-(2-methoxy-1,4-benzodioxanyl)]-2-imidazoline and four parts microcrystalline cellulose together with 1% of magnesium stearate is compressed into tablets. Conveniently the tablets are of such a size as to contain 1, 5, 10 or 25 mg of the active ingredient.

EXAMPLE II

A mixture of one part 2-[2-(2-methoxy-1,4-benzodioxanyl)]-2-imidazoline and four parts spray dried lactose together with 1% magnesium stearate is filled into hard gelatine capsules. The capsules may conveniently contain 1, 5, 10 or 25 mg of the active ingredient.

We claim:
1. A compound of the formula

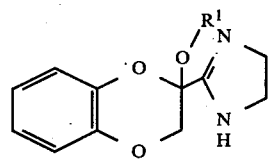

wherein $R^1$ is alkyl $C_{1-4}$, allyl, benzyl, phenethyl or hydroxyalkyl $C_{2-4}$ and its non-toxic salts, having the RS or S configuration.

2. 2-[2-(2-Methoxy-1,4-benzodioxanyl)]-2-imidazoline.

3. 2-[2-(2-Ethoxy-1,4-benzodioxanyl)]-2-imidazoline.

4. (S)-2-[2-(2-Methoxy-1,4-benzodioxanyl)]-2-imidazoline.

5. A compound according to claim 1 which is selected from the group consisting of
2-[2-(2-i-propoxy-1,4-benzodioxanyl)]-2-imidazoline,
2-[2-(2-n-propoxy-1,4-benzodioxanyl)]-2-imidazoline,
2-[2-(2-n-butoxy-1,4-benzodioxanyl)]-2-imidazoline,
2-[2-(2-allyloxy-1,4-benzodioxanyl)]-2-imidazoline,
2-[2-(2-benzyloxy-1,4-benzodioxanyl)]-2-imidazoline,
2-[2-(2-phenylethoxy-1,4-benzodioxanyl)]-2-imidazoline,
2-[2-(2-hydroxyethoxy-1,4-benzodioxanyl)]-2-imidazoline,
2-[2-(2-hydroxybutoxy-1,4-benzodioxanyl)]-2-imidazoline,
and their non-toxic salts.

6. A pharmaceutical composition for presynaptic $\alpha_2$-adrenoreceptor antagonist use comprising a compound as claimed in claim 1, or a non-toxic salt thereof in an amount effective for said use together with a pharmaceutically acceptable diluent or carrier.

7. A pharmaceutical composition as claimed in claim 6 which is in unit dosage form.

8. A pharmaceutical composition as claimed in claim 7 for oral administration wherein each unit dosage contains from 1 to 200 mg of the compound of formula I or a non-toxic salt thereof.

9. A pharmaceutical composition as claimed in claim 8 wherein each unti dosage contains from 5 to 50 mg of the compound of formula I or a non-toxic salt thereof.

10. A pharmaceutical composition as claimed in claim 7 for parenteral administration wherein each unit dosage contains from 0.1 to 10 mg of the compound of formula I or a non-toxic salt thereof per 1 ml of the composition.

11. A method of treating depression which comprises administering to a human an antidepressant effective amount of a compound as claimed in claim 1 or a non-toxic salt thereof.

* * * * *